(12) United States Patent
Banerjee

(10) Patent No.: US 6,841,390 B1
(45) Date of Patent: Jan. 11, 2005

(54) METHOD FOR SENSING STICKIES

(75) Inventor: Sujit Banerjee, Marietta, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 471 days.

(21) Appl. No.: 10/011,992

(22) Filed: Nov. 29, 2001

Related U.S. Application Data

(60) Provisional application No. 60/253,850, filed on Nov. 29, 2000.

(51) Int. Cl.[7] ................................................. D21C 5/02
(52) U.S. Cl. .......................... 436/146; 436/52; 436/166; 162/4; 162/49
(58) Field of Search .................... 436/52–53, 145–146, 436/166; 162/4, 49, 162, 198

(56) References Cited

U.S. PATENT DOCUMENTS 4,758,308 A * 7/1988 Carr ............................ 162/263
6,589,427 B2 * 7/2003 Moghe et al. ............... 210/667

OTHER PUBLICATIONS

Ortner et al., Process Technological Solutions for the Separation of Sticky Impurities, Tappi Press, 1983 book 3, pp. 695–701.*

Doshi et al., Detection and Quantification of Sticky Contaminants in Recycled Fiber Systems, Tappi Press, 1983 book 2, pp. 703–707.*

Krueger et al., Removing 'Stickies'from Recycled Fiber, Tappi Press, 1981 vol. 64 No. 7, pp. 39–41.*

* cited by examiner

Primary Examiner—Lyle A. Alexander
(74) Attorney, Agent, or Firm—Veda V. Cherry, Esq.

(57) ABSTRACT

A real-time system and method for measuring stickies by separating high molecular weight non-fibrous species from low molecular weight non-fibrous species and sensing the concentration of the high molecular weight species. Specifically, a fiber slurry containing stickies is filtered to remove fibers, fiber debris, and other large contaminant particles from the fiber slurry, after which the carbon content of the filtered sample is measured. Next, the filtrate is ultrafiltered to separate stickies having a high molecular weight from the filtrate, and subsequently, the carbon content of the ultrafiltered sample is measured. Finally, the carbon contents are used to determine the microstickies concentration in the fiber slurry.

15 Claims, 5 Drawing Sheets

METHOD FOR SENSING STICKIES

CROSS REFERENCE TO RELATED APPLICATIONS

This is a non-provisional application claiming the benefit of U.S. Provisional Application Ser. No. 60/253,850, filed Nov. 29, 2000, which is incorporated herein by reference.

FIELD OF THE INVENTION

The present invention generally relates to the art of sensing high molecular weight non-fibrous species in a process stream, and more particularly pertains to sensing stickies in a fiber slurry, such as a virgin pulp slurry or secondary fiber slurry.

BACKGROUND OF THE INVENTION

People throughout our society have become increasingly aware and concerned about the environmental issues that plague the world. The depletion of the ozone layer, the rain forests, and clean water are just a few of the environmental issues that are being addressed. One approach in addressing these issues includes preserving resources by recycling them. Consequently, the recycling industry has become instrumental to serving this need.

In the recycling field, one area of increasing interest is the reuse of wastepaper. Millions of tons of wastepaper are generated every year in the United States. Recycling this wastepaper can save countless trees, as well as provide other ecological and economic benefits. However, the key to reuse of this wastepaper is the removal of contaminants from the wastepaper, thereby facilitating the use of recycled or secondary fibers from the wastepaper.

The paper recycling industry encounters a variety of contaminants in wastepaper. Many of these contaminants adhere to paper fibers and therefore may cause problems during the recycling process. One such contaminant is "stickies", which can come from synthetic and natural sources. Stickies typically are classified as hot melts, pressure-sensitive adhesives (PSAs), latexes, binders, pitch, and ink and combinations thereof. Stickies can also be classified as macrostickies or microstickies depending upon the size of the stickies.

Stickies may cause operational and product quality problems. Stickies can deposit on machine surfaces, such as wires, felts, press rolls, and drying cylinders, cause process upsets, hinder fiber bonding, and reduce product quality. Consequently, it is necessary to monitor and control stickies to improve papermaking operations and product quality.

The paper industry typically uses mechanical methods of dispersion, screening and cleaning for controlling stickies. Screens and centrifugal cleaners are typically used to remove or separate stickies and other debris from the process stream. Nevertheless, stickies still may be found in the process stream. These remaining stickies may be controlled through use of minerals such as talc or surface-active chemicals for modification, detackification, or pacification of the stickies. These minerals and chemicals contribute significantly to operating costs.

Macrostickies are stickies that are large enough to be screened out during the conventional screening process using, for example, a 0.0006" screen. Macrostickies are most commonly monitored using a device know as a "Pulmac shive analyzer," which screens out the macrostickies from the furnish and determines the macrostickies level through image analysis. This process usually takes several hours to complete, and is useful as an "after-the-fact" record of the macrostickies level. However, owing to the long analysis time required, this process cannot provide feedback during the pulping process such that actions can be initiated to respond to high stickies levels. Consequently, there are no reliable prior art methods for rapidly monitoring stickies levels in an incoming furnish.

Microstickies are small enough to traverse the screening and cleaning systems, and are principally responsible for operational and product quality problems. However, there does not appear to be any prior methods or devices for sensing microstickies.

Therefore, there is a need for a system and method for rapidly sensing microstickies. There is also a need for a system and method for monitoring microstickies levels such that the use of minerals and chemicals can be minimized during normal operations, and increased when an outbreak of microstickies occurs. There is yet another need for a system and method for sensing microstickies that can be performed easily and efficiently.

SUMMARY OF THE INVENTION

The present invention solves the above-described needs by providing a system and method for measuring stickies by separating high molecular weight non-fibrous species from low molecular weight non-fibrous species and sensing the concentration of the high molecular weight species.

Generally, an improved method for measuring stickies comprises the steps of providing a sample containing stickies; filtering the sample to remove materials of a predetermined size from the sample; measuring the amount of carbon in the filtered sample; ultrafiltering the filtered sample to separate stickies having a predetermined molecular weight from the filtered sample; measuring the amount of carbon in the ultrafiltered sample; and determining the difference between the amounts of carbon in the filtered and the ultrafiltered samples to obtain a measure of stickies. The sample can be a fiber slurry, such as a virgin pulp slurry or a secondary fiber slurry.

The stickies typically are selected from a group consisting of pressure sensitive adhesives, hot melts, binders, ink, pitch and combinations thereof. The stickies are predominantly microstickies. The stickies usually have a molecular weight ranging from about 1000 Da to 10,000 Da. Further, the stickies can have a molecular weight of at least 3000 Da or greater.

The step of filtering the sample comprises coarse filtering out the materials of a predetermined size from the sample. The materials of a predetermined size can be selected from a group consisting of fiber, fiber debris, particulate matter being at least 25 microns, and combinations thereof. In an on-line system, the step of ultrafiltering can use a membrane having a molecular weight cut-off ranging from about 1000 Da to 10,000 Da. Further, the membrane can have a molecular weight cut-off of about 3000 Da.

In a laboratory system, the step of ultrafiltering the filtered sample can use a filter paper having the same molecular weight cut-offs as the on-line system.

In another embodiment, a method for rapidly measuring the concentration of a high molecular weight non-fibrous species in a process stream is described, comprising the steps of (a) providing a process stream containing fibrous species and non-fibrous species, said non-fibrous species having high molecular weights and low molecular weights; (b) filtering the process stream to remove the fibrous species from the process stream; (c) measuring the total organic carbon content in the filtered process stream containing the non-fibrous species; (d) ultrafiltering the filtered process stream to separate the non-fibrous species having the high molecular weights from the non-fibrous species having the low molecular weights; (e) measuring the total organic carbon content in the ultrafiltered process stream containing the non-fibrous species having the low molecular weights; and (f) correlating the difference between the total organic carbon content measured in step (c) and the total organic carbon content measure in step (e) to the high molecular weight non-fibrous species, thereby determining the concentration of high molecular weight non-fibrous species in the process stream.

The high molecular weights can range from about 1000 Da to 10,000 Da, and further, can be at least 3000 Da or greater.

The high molecular weight non-fibrous species is predominantly stickies. The total organic carbon contents in the filtered process stream and ultrafiltered process stream can be measured using a total organic carbon analyzer. The entire process (a) through (f) can be completed within 30 minutes, and can be performed prior to the process stream entering a paper machine chest.

In another embodiment, a system for monitoring microstickies levels is described, comprising: a filter immersed in a fiber slurry removing materials of a predetermined size from the fiber slurry; an ultrafilter immersed in the fiber slurry separating microstickies having a predetermined molecular weight from the fiber slurry; and a carbon analyzer submerged in the fiber slurry first measuring the amount of carbon in the fiber slurry after filtration of the materials and second measuring the amount of carbon in the fiber slurry after ultrafiltration of the microstickies so that the carbon values obtained can be used to determine microstickies levels.

A microstickies processor can be functionally connected to the total organic carbon analyzer, said microstickies processor processing said first and second measurements obtained from the total organic carbon analyzer to determine the level of microstickies in the fiber slurry.

The filter can be a filter capable of filtering out materials being at least 25 microns, such as a Whatman #4 paper. The carbon analyzer is a total organic carbon analyzer for measuring the total organic carbon of the fiber slurry.

The predetermined molecular weight of the microstickies is in the range of about 1000 Da to 10,000 Da, and further, can be at least 3000 Da or greater.

The microstickies processor processes said first and second measurements by determining the difference between the first and second measurements, thereby determining the level of microstickies in the fiber slurry.

In another embodiment of the present invention, a method for sensing dissolved or suspended species having high molecular weights in a secondary fiber stream, comprises the steps of:
providing a secondary fiber stream containing species of varying molecular weights and species larger than 25 microns; filtering the stream through a first medium (filtrate), where the first medium retains species larger than 25 microns; ultrafiltering the stream through a second medium (permeate), where the second medium retains species of molecular weights greater than 3,000 daltons; measuring the total organic carbon contents in the filtrate and the permeate; and relating the difference between the total organic carbon contents to species having molecular weights greater than 3,000 daltons in the secondary fiber stream.

The present invention provides the benefit of sensing microstickies in real-time, so as to facilitate regulation of the amount of chemicals and minerals used to neutralize stickies. Such regulation can provide substantial cost savings while preserving product quality and machine runnability.

These and other objects, features, and advantages of the present invention may be more clearly understood and appreciated from a review of the following detailed description of the disclosed embodiments and by reference to the appended drawings and claims.

DETAILED DESCRIPTION

The present invention describes a real-time system and method for measuring stickies, specifically microstickies, in a process stream. Stickies typically are classified as hot melts, including polyvinyl acetate and ethlylene vinyl acetate, pressure-sensitive adhesives (PSAs), such as acrylates and other polymers used as adhesives, in addition to latexes, binders, pitch, and ink. Further, stickies can be classified based on size into macrostickies or microstickies.

The basis of the method lies in the determination that non-fibrous species of a high molecular weight dissolved or suspended in a fiber slurry after using conventional screening methods are predominantly stickies. Other high molecular weight compounds, such as dispersants, which may be present in the fiber slurry, are represented in very low concentrations, and are therefore, negligible when it comes to measuring stickies concentrations. Chemicals, like alkali and surfactants, typically are added to the fiber slurry stock prior to screening, but these chemicals either have a lower molecular weight or are present at very low levels, and therefore, are also negligible. Furthermore, low molecular weight non-fibrous species found in the process stream have been determined not to be stickies, and therefore, if separated from the high molecular weight stickies, stickies levels then can be measured.

In general, the present application describes a system of separating high molecular weight non-fibrous species from low molecular weight non-fibrous species in a process stream and sensing the concentration of the high molecular weight species in the process stream. This inventive system can be performed quickly and efficiently such that corrective action for controlling stickies can be taken. Moreover, the inventive process can be performed either on-line in the mill environment or off-line as in a laboratory setting.

The present invention not only provides the benefit of a real-time measure of stickies, but also serves as an early warning system for detecting a bad batch during production in the mill environment. In addition, the present invention provides a map of where stickies are located in the mill, thereby providing information as to where and what level stickies problems can be expected. Further, such information can aid in the determination of the amount of chemicals and minerals needed to neutralize stickies, resulting in substantial cost savings due to reduced chemical and mineral usage.

Exemplary embodiments of the present invention are described herein below in connection with FIGS. 1–5, wherein like numerals represent like elements among the figures, and the accompanying examples.

Figure 1:
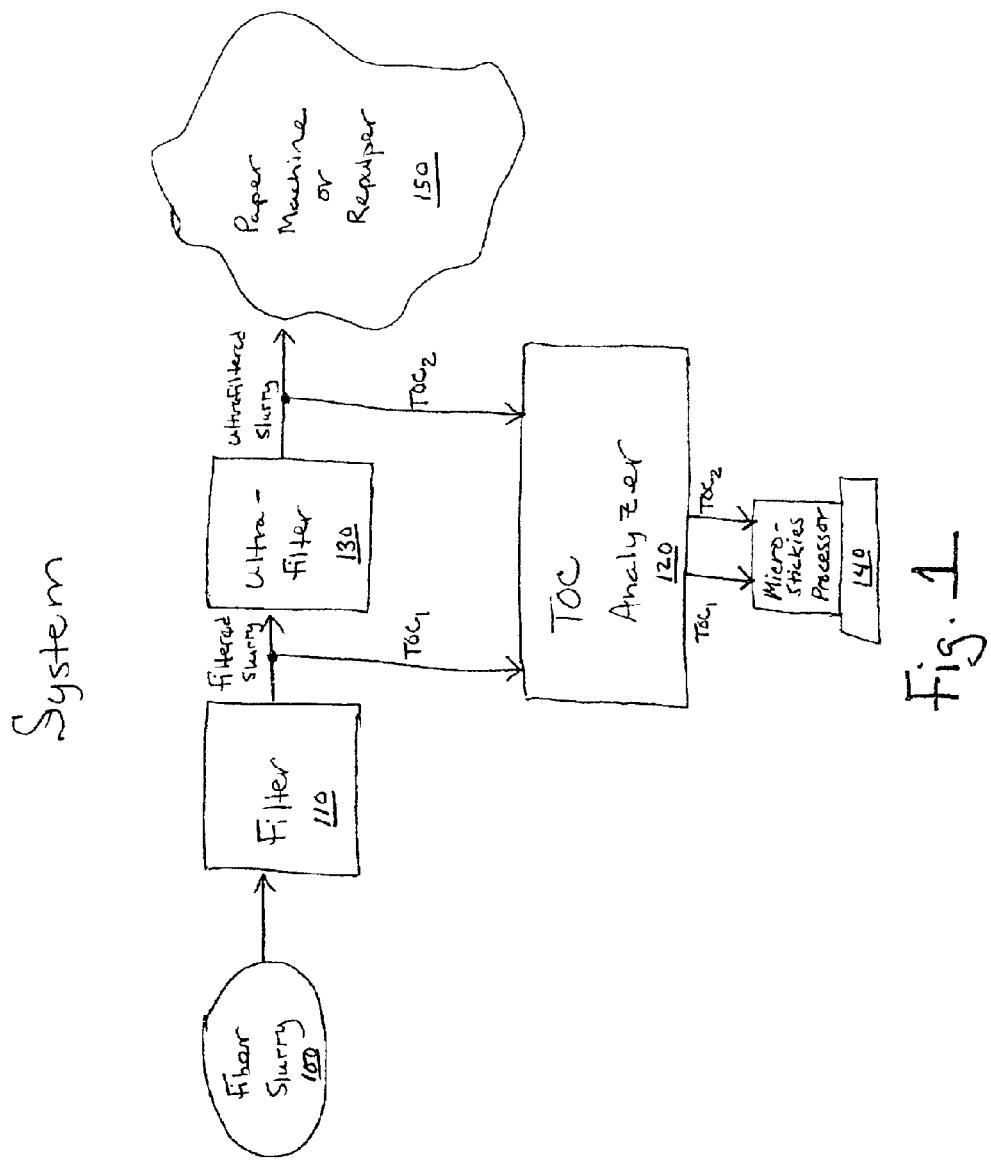
FIG. 1 is a block diagram illustrating a system for sensing stickies in accordance with an exemplary embodiment of the present invention.

Referring to FIG. 1, an inventive system for sensing stickies dissolved or suspended in a process stream is illustrated. A process stream as referred to herein can be a virgin pulp slurry, a secondary fiber slurry, or other fiber slurry. In FIG. 1, a fiber slurry 100 containing stickies is filtered using a filter 110 to remove fiber, fiber debris, large contaminant particles, and other particulate matter. For instance, substances found in the process stream that are larger than about 25 microns can be filtered out. This can be accomplished by coarse filtering the fiber slurry 100 through filter paper, such as Whatman #4 or an equivalent.

The amount of carbon in the filtered sample, i.e. the filtrate, is then measured with a total organic carbon (TOC) analyzer 120 to obtain the total organic carbon ($TOC_1$) load of the filtered sample. This TOC value is measured in parts per meter (ppm). One such TOC analyzer is manufactured by Ionics Corporation of Watertown, Mass., Model 1555B. However, any device suitable for measuring carbon can be used.

After obtaining the carbon content of the filtrate, an ultrafilter 130 is used to separate high molecular weight non-fibrous species, namely stickies, from low molecular weight non-fibrous species in the filtrate. The ultrafilter 130 can be a membrane with a molecular weight cut-off of about 1000 Da to about 10,000 Da. Further, the membrane can have a molecular weight cut-off of about 3,000 Da. One such membrane is manufactured by PCI Membranes of Milford, Ohio. This membrane can be an open tube that filters out liquids that flow through it or any other filtering device known to those skilled in the art. In a lab model, a conventional filter paper may be used for ultrafiltration instead of a membrane. One skilled in art will appreciate that any screening or filtering device capable of separating high and low molecular weight substances from each other can be used in an on-line or off-line embodiment of the present invention.

As a result of ultrafiltration at the preferred level of about 3000 Da, stickies, and more particularly microstickies, cannot penetrate the ultrafilter 130 due to the thickness of the ultrafilter and the high molecular weight of stickies. It will be appreciated by one skilled in the art that the molecular weight of stickies is typically in a range of about 1000 Da to about 10,000 Da, and more typically is about 3000 Da. By using the appropriate ultrafilter 130, the ultrafiltered sample, i.e. the permeate, should contain primarily the low molecular weight non-fibrous species.

The amount of carbon in the permeate is then measured with the TOC analyzer 120 to obtain the total organic carbon ($TOC_2$) load of the permeate. This $TOC_2$ value represents the low-molecular weight (i.e. <3,000 Da) component of the $TOC_1$.

A microstickies processor 140 can be used to perform an analytical technique for determining the level of stickies in the fiber slurry. This technique takes the difference between the $TOC_1$ and $TOC_2$ measurements, which yields the high molecular weight TOC of the stickies in the fiber slurry. This high molecular weight TOC is proportional to the stickies concentration, which is expressed on a per carbon basis. One skilled in the art will appreciate that the present invention is not limited to use of a processor for determining stickies levels, but may instead use other conventional methods of making such a determination, such as manual calculations, charts, and so forth.

Once the stickies level is determined, which can be done in a matter of a few minutes, this information can be used to decide how the stickies will be treated prior to entry into the paper machine or repulper 150.

Figure 2:
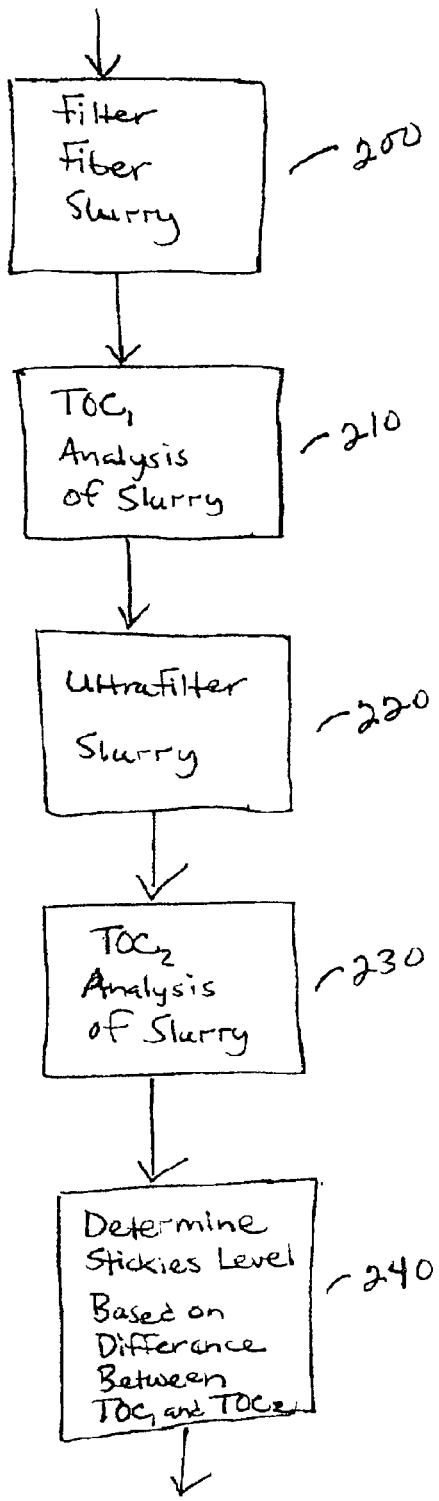
FIG. 2 is a flow diagram illustrating a process for sensing stickies in accordance with an exemplary embodiment of the present invention.

Now turning to FIG. 2, a process for measuring stickies is described. In step 200, a fiber slurry containing stickies is filtered to remove materials of a predetermined size, such as fibers, fiber debris, and other large contaminant particles, from the fiber slurry. Next, in step 210, a TOC analysis of the sample is performed to determine the amount of carbon in the sample. The sample is then ultrafiltered, a previously described, to separate species having a predetermined molecular weight, which can be greater than 3000 Da, from the sample in step 220. Another TOC analysis is performed in step 230 to determine the amount of carbon in the sample after ultrafiltration. Finally, in step 240, the stickies level is determined based on the difference between the amounts of carbon in the filtered sample and the ultrafiltered sample.

The following examples, which are merely illustrative of the present invention, further demonstrate application of the present invention, as well as demonstrate the benefits associated therewith.

Example 1

Based on the prior art method of determining the tack of material to measure stickies, a filtrate was boiled down from 700 ml to 5 ml. 1 ml of the filtrate was plated on a metal surface, dried, and a standard tack test was performed as a function of temperature. The tack was then normalized to 40° C. Several measurements were made at various mills using this process, which took several hours to complete for each test.

Figure 3:
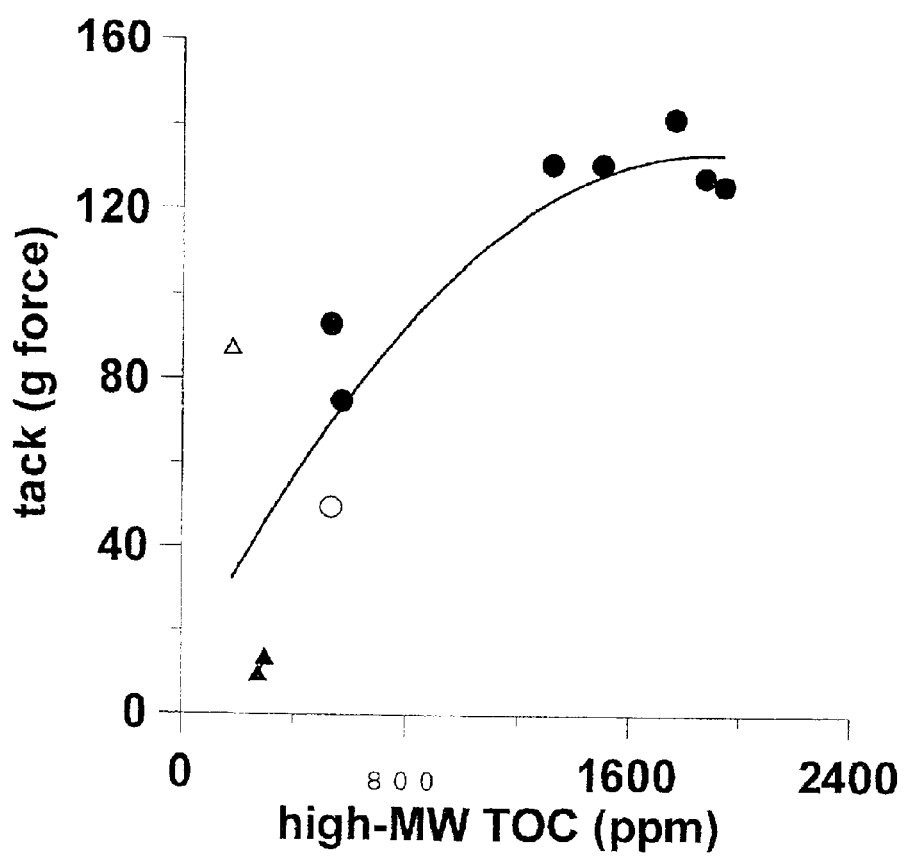
FIG. 3 is a graph illustrating the connection between tack vs. the total organic carbon value of a high molecular weight non-fibrous species in accordance with an exemplary embodiment of the present invention.

The inventive process as described in connection with FIGS. 1 and 2 was used to measure stickies at the same mills. The process of the present invention took less than 5 minutes to perform each test. FIG. 3 is a graphical illustration of the results of these experiments showing the relationship between tack and high molecular weight TOC.

In FIG. 3, there is a continuous relationship between tack and the high-MW TOC values. In other words, the tack can be estimated from the graph from the high-MW measurement. The high-MW TOC value is clearly related to tack and can act as a surrogate for it. Since the tack derives only from the stickies in the sample, the high-MW TOC is, therefore, a measure of stickies. Each symbol in the graph represents a different mill, and the relationship between tack and high-MW TOC is valid across several mills, and is a general and useful relationship.

Example 2

Initial laboratory work showed that when Carbotac (a typical pressure sensitive adhesive from B. F. Goodrich used in the industry) was homogenized, suspended in water, and ultrafiltered. Twenty-percent of the amount of the TOC in the sample was found in the ultrafiltered fraction, which means that 80% of the Carbotac initially added was present in the high molecular fraction and was correctly identified as stickies.

Samples were then taken from several process streams in a newsprint mill utilizing secondary fiber, and processed in the following sequence. Each stream was filtered and the TOC of the filtrate was measured. The same stream was ultrafiltered and the TOC of the permeate was determined. The difference between the two readings was the high molecular weight fraction and was ascribed to stickies. The results of this experiment are shown in FIG. 4.

Figure 4:
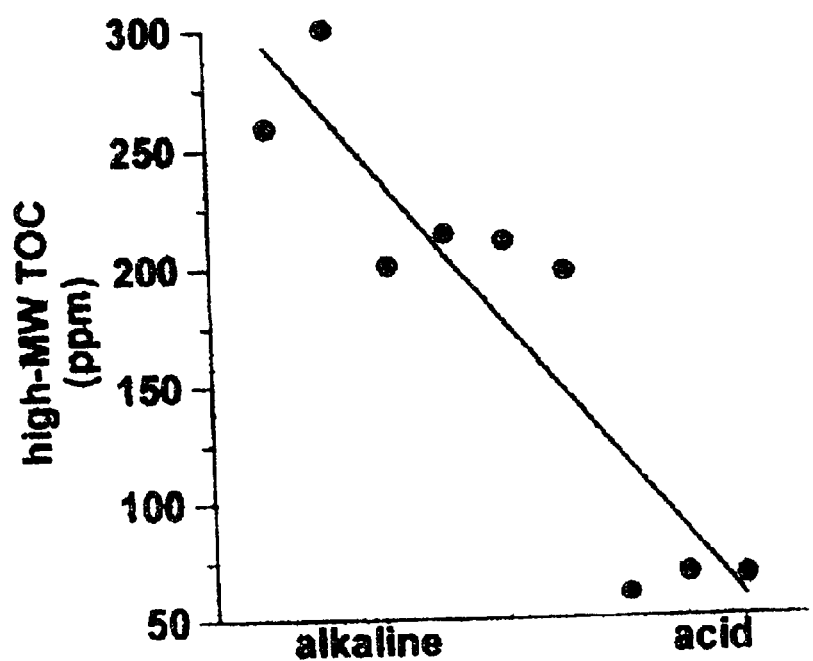
FIG. 4 is a graph illustrating the high molecular weight TOC values of samples taken from process streams of a secondary fiber newsprint mill in accordance with an exemplary embodiment of the present invention.

FIG. 4 is a graphical illustration of the high molecular weight TOC values of samples taken from process streams of the secondary fiber newsprint mill. In FIG. 4, the unit operations progress from the left side of the plot to the right, where the "pulper accepts" represent a stream early in the process and the "feed to the paper mill" represents a stream late in the process. Specifically, the sampling points from left to right are pulper accepts, feed to coarse screens, feed to fine screens, feed to alkaline flotation cell, feed to alkaline DNT washers, feed to alkaline press accepts, feed to flotation cell, feed to HD storage, feed to LD storage, and feed to paper mill. As observed in FIG. 4, it is expected that the various screening and cleaning operations would reduce the stickies that are represented by "high molecular weight TOC" to a small value in the "feed to the paper mill."

Example 3

Figure 5:
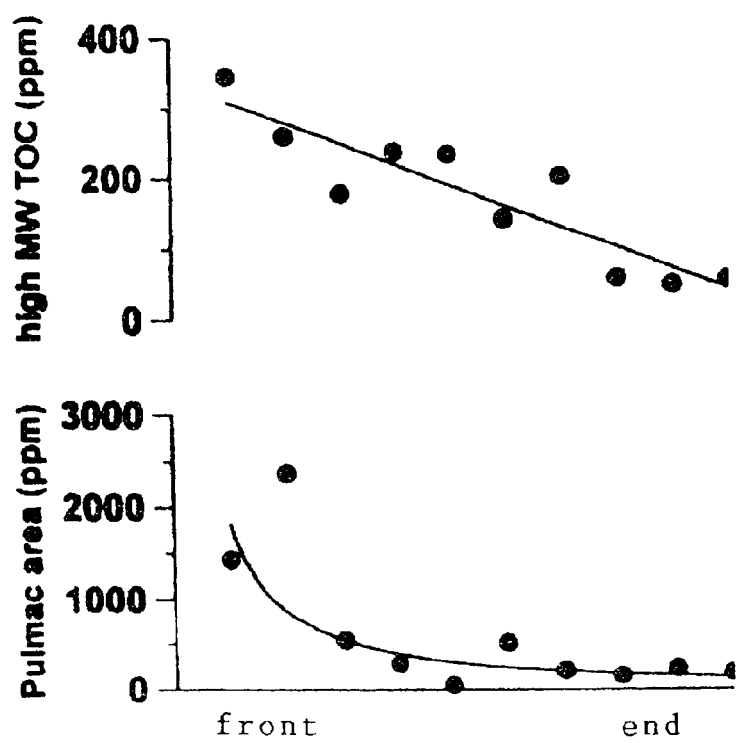
FIG. 5 is a graph illustrating the Pulmac/TOC profiles from a paper mill in accordance with an exemplary embodiment of the present invention.

FIG. 5 compares results from conventional analysis with a Pulmac device and with the method of the present invention of a paper mill stream. The number of unit operations used to clean the pulp increases along the abscissa. The Pulmac device measures macrostickies, and it is evident that the macrostickies are removed early in the process. However, the present invention shows that a considerable quantity of microstickies remains after the macrostickies are removed. It is clear that the Pulmac device does not provide a measure of the total quantity of microstickies.

Alternative embodiments will become apparent to those skilled in the art to which the present invention pertains without departing from its spirit and scope. Accordingly, the scope of the present invention is defined by the appended claims rather than the foregoing description.

What is claimed is:

1. An improved method for measuring stickies, comprising the steps of:
   providing a sample containing stickies;
   filtering the sample to remove materials of a predetermined size from the sample;
   measuring the amount of carbon in the filtered sample;
   ultrafiltering the filtered sample to separate stickies having a predetermined molecular weight from the filtered sample;
   measuring the amount of carbon in the ultrafiltered sample; and
   determining the difference between the amounts of carbon in the filtered sample and the ultrafiltered sample to obtain a measure of stickies.

2. The method of claim 1, wherein the stickies are selected from a group consisting of pressure sensitive adhesives, hot melts, binders, ink, pitch and combinations thereof.

3. The method of claim 1, wherein the stickies are predominantly microstickies.

4. The method of claim 1, wherein the stickies have a molecular weight ranging from about 1000 Da to 10,000 Da.

5. The method of claim 1, wherein the stickies have a molecular weight of at least 3000 Da.

6. The method of claim 1, wherein the stickies have a molecular weight greater than 3000 Da.

7. The method of claim 1, wherein the sample is a fiber slurry.

8. The method of claim 7, wherein the fiber slurry is a virgin pulp slurry.

9. The method of claim 7, wherein the fiber slurry is a secondary fiber slurry.

10. The method of claim 1, wherein the step of filtering the sample comprises coarse filtering out the materials of a predetermined size from the sample.

11. The method of claim 1, wherein the materials of a predetermined size are selected from a group consisting of fiber, fiber debris, particulate matter being at least 25 microns, and combinations thereof.

12. The method of claim 1, wherein the step of ultrafiltering the filtered sample comprises filtering the filtered sample through a membrane having a molecular weight cut-off ranging from about 1000 Da to 10,000 Da.

13. The method of claim 12, wherein the membrane has a molecular weight cut-off of about 3000 Da.

14. The method of claim 1, wherein the step of ultrafiltering the filtered sample comprises filtering the filtered sample through a filter paper having a molecular weight cut-off ranging from about 1000 Da to 10,000 Da.

15. The method of claim 14, wherein the filter paper has a molecular weight cut-off of about 3000 Da.

* * * * *